United States Patent [19]

Moore

[11] Patent Number: Plant 6,468

[45] Date of Patent: Dec. 13, 1988

[54] MINIATURE ROSE PLANT

[75] Inventor: Ralph S. Moore, Visalia, Calif.

[73] Assignee: Sequoia Nursery, Visalia, Calif.

[21] Appl. No.: 6,782

[22] Filed: Jan. 27, 1987

[51] Int. Cl.[4] ..... A01H 5/00

[52] U.S. Cl. ..... Plt./26

[58] Field of Search ..... Plt./26–27

*Primary Examiner*—Robert E. Bagwill

[57] ABSTRACT

This invention relates to a new and distinct variety of Floribunda rose plant primarily identified by its large, few petaled (single) flowers and unique pink blend coloring.

1 Drawing Sheet

The present invention relates to a new and distinct variety of hardy, bush type rose plant of the Floribunda class; the variety being primarily characterized — as to novelty — by the few petaled (single) flowers, long slender buds and unique blending of color.

The variety is further characterized by:

An abundance of bloom, with flowers usually borne several to the stem in loose clusters of 3 to 5 or more. Some fragrance.

A plant which is vigorous, of rounded, to spreading shape with fairly large glossy to semi-glossy foliage with pointed leaflets; the buds and flowers being similar in form to Dainty Bess (Hybrid Tea — not patented).

The plant, which has a normal height of 30 inches (78 cm) or more, can easily be maintained at lesser height by occasional trimming.

A plant which grows and blooms satisfactorily both in greenhouse and outdoors; is good for growing in the garden or large containers (tubs) and provides excellent garden decoration as well as flowers for bouquets and exhibition.

The present variety of Floribunda rose was originated by me at Sequoia Nursery, located at Visalia, Calif., under conditions of careful control and observation, as a cross between Playboy (Floribunda — not patented) as the seed parent and Angel Face (Floribunda — U.S. Plant Pat. No. 2,792) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of Floribunda rose plant, the following is a detailed description thereof in outline; all major color plate identifications being by reference to the British Colour Council Horticultural Colour Chart, except where common terms of color definition are employed.

Type: Hardy; bushy; rounded; seedling; outdoors; cut flowers; garden decoration; exhibition.

Class: Floribunda. Variety identification: MORplag (Commercial synonym: Playgirl).

Flowers borne: Usually several together (3 to 5 or more) on sturdy, wirey stems.

Quantity of bloom: Abundant all season.

Bud:

*Peduncle.*—Medium to long; slender but sturdy; erect; medium green, sometimes tinted bronze (outdoors); usually quite smooth. Before calyx breaks; medium size (18–20 mm long).

*Form.*—Long pointed, with few foliaceous appendages and hairs on surface of bud; with foliaceous parts extending beyond the tip of the bud equal to less than one-half of its length.

*Color.*—Medium green, occasionally tinted with bronze (outdoors). As calyx breaks, color — deep pink to red (near Spirea Red 025 or similar). Opening: Opens well in all weather.

Bloom:

*Size when fully open.*—Large, averaging about 9 cm (3½").

*Petalage.*—Few — averaging about 5–7 petals, arranged regularly.

*Form.*—Open, with slightly ruffled petals. Open flowers show stamens.

Petals: Fairly thick; satiny on inside and on outside surface.

*Shape.*—Outside petals, broad lanceolate (nearly round) with rounded tip, the petals being wavey (Sweet pea-like) with often serrated edges.

Color: Newly opened flower from a plant grown outdoors (November 1986), Visalia, Calif.

*Outside petal.*—Outside surface — near Spirea Red 025 or 025/1 with darker veins; with small yellow area at base. Inside surface — near Spirea Red 025 with lighter veining; with bright yellow area at base. Opening and freshly opened flowers may have slightly darker veining (in warmer weather and brighter light, buds and flowers are lighter in color — similar to Solferino Purple 26/1 or lighter). Note: This flower is a pink-/lavender blend, difficult to capture on photo film. Three days open — color — similar to fresh open flower, but less bright. Behavior — opens well in all weather. Spent petals drop off. Flower longevity (July–August 1986) — plant in garden 5–6 days or longer. Cut flowers at living room temperature 3–5 days.

Reproductive organs:

*Stamens.*—Many.

*Filaments.*—Slender; reddish.

*Anthers.*—Well developed; yellow.

*Pollen.*—Fairly abundant.

*Pistils.*—Numerous.

*Styles.*—Fairly uniform; yellowish, bunched.

*Ovaries.*—All enclosed in calyx.

*Hips.*—Several.

*Sepals.*—Permanent; spear shaped; recurved.

*Seed.*—Fair amount.

Foliage:

*Leaves.*—Compound of five (sometimes three or seven) leaflets; large; leathery; semi-glossy to glossy.

*Leaflets.*—Shape: broad; lanceolate; apex acute; base — rounded. Color: medium green; new growth — normal (medium) green often tinted reddish. Rachis: medium strength; upperside may have a few short hairs; grooved; underside may have several small thorns (or claws) and few to several tiny short prickles. Stipules: short length; medium width; medium to short length narrow points which turn out usually at about 45 degrees.

Growth:

*Habit.*—Dwarf; bushy; rounded; much branched.

*Growth.*—Vigorous; internodes fairly short.

*Canes.*—Medium; slender sturdy.

*Main stems.*—Color; medium green.

*Thorns.*—Average, of medium size and length — usually straight. Hairs — few or none.

The Floribunda rose plant and its flowers as herein described may vary in slight detail due to climatic, soil and cultural conditions under which the variety may be grown; the present description being of the variety as grown at Visalia, Calif.

The following is claimed:

1. A new and distinct variety of rose plant of the Floribunda class, of hardy, dwarf, bushy, rounded, much branched habit, substantially as illustrated and described, characterized by buds and flowers of an unusual pink/lavender blend, the bud being pointed and quite slender in the early opening stages, with the open flower being single with 5–7 wavey petals, and further characterized by a plant of compact, vigorous, well rounded shape, with main stems and shoots, moderately thorny, the said plant being easy to propagate from soft wood cuttings and by budding, with an abundance of large semi-glossy to glossy foliage, the flowers usually being borne several together in loose clusters on medium length stems.

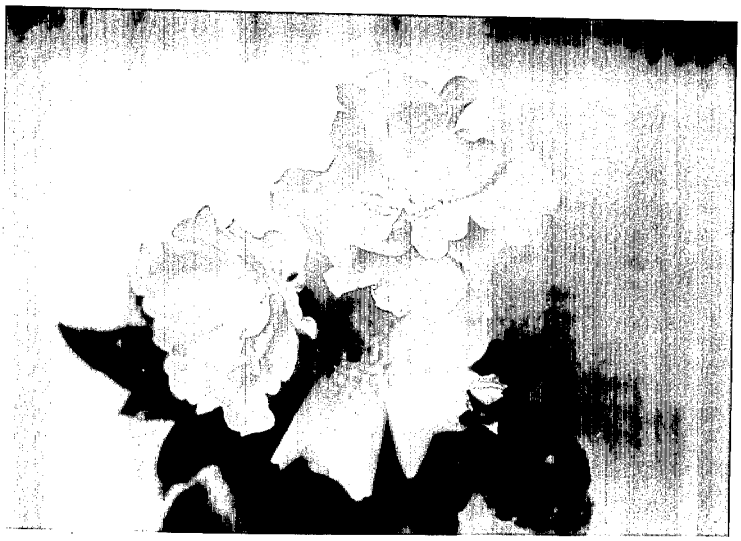

* * * * *